United States Patent
Geist

(10) Patent No.: US 9,463,052 B2
(45) Date of Patent: Oct. 11, 2016

(54) ACCESS ASSEMBLY FOR ANTERIOR AND LATERAL SPINAL PROCEDURES

(71) Applicant: Integrity Implants Inc., Cooper City, FL (US)

(72) Inventor: Wyatt Drake Geist, Davie, FL (US)

(73) Assignee: Integrity Implants Inc., Cooper City, FL (US)

( * ) Notice: Subject to any disclaimer, the term of this patent is extended or adjusted under 35 U.S.C. 154(b) by 125 days.

(21) Appl. No.: 13/739,805

(22) Filed: Jan. 11, 2013

(65) Prior Publication Data

US 2013/0184771 A1    Jul. 18, 2013

Related U.S. Application Data

(60) Provisional application No. 61/585,724, filed on Jan. 12, 2012.

(51) Int. Cl.
*A61B 17/70* (2006.01)
*A61B 17/17* (2006.01)
*A61B 17/02* (2006.01)

(52) U.S. Cl.
CPC ....... *A61B 17/7074* (2013.01); *A61B 17/1757* (2013.01); *A61B 17/708* (2013.01); *A61B 2017/0256* (2013.01)

(58) Field of Classification Search
CPC ...... A61F 2/46; A61F 2/4601; A61F 2/4603; A61F 2/4611
USPC ............... 606/246, 279, 86 A, 86 R, 105
See application file for complete search history.

(56) References Cited

U.S. PATENT DOCUMENTS

| | | | | |
|---|---|---|---|---|
| 3,750,667 A | * | 8/1973 | Pshenichny et al. | 604/117 |
| 4,580,563 A | * | 4/1986 | Gross | 606/79 |
| 5,013,318 A | * | 5/1991 | Spranza, III | 606/102 |
| 5,484,437 A | * | 1/1996 | Michelson | 606/86 A |
| 5,741,253 A | * | 4/1998 | Michelson | 606/86 A |
| 6,063,088 A | * | 5/2000 | Winslow | 606/86 A |
| 6,228,022 B1 | * | 5/2001 | Friesem et al. | 600/204 |
| 6,283,966 B1 | * | 9/2001 | Houfburg | 606/914 |
| 6,506,151 B2 | * | 1/2003 | Estes et al. | 600/226 |

(Continued)

FOREIGN PATENT DOCUMENTS

WO      WO0217206      2/2002

OTHER PUBLICATIONS

Unger and Kowitt, "Fight back—iPhone application to fight florida traffic ticket.", Internet article: http://udm4.com/iPhone/Fight_Back_Florida_T-3957004, (retrieved Mar. 18, 2013).

(Continued)

*Primary Examiner* — Eduardo C Robert
*Assistant Examiner* — Michelle C Eckman
(74) *Attorney, Agent, or Firm* — McHale & Slavin, P.A.

(57) ABSTRACT

Briefly, the present invention is directed to methods and instrumentation for performing surgery on the spine along its lateral aspect (side) and generally by a lateral, anterior or an anterolateral surgical approach, such that the instruments enter the body from an approach that is other than posterior and make contact with the spine along its lateral aspect. The present invention provides for the entire surgical procedure to be performed through a relatively small incision and may be performed in either the thoracic or lumbar spine.

16 Claims, 14 Drawing Sheets

(56) References Cited

U.S. PATENT DOCUMENTS

| | | | |
|---|---|---|---|
| 6,589,247 B2* | 7/2003 | McGahan et al. | 606/90 |
| 6,740,091 B2* | 5/2004 | Kohrs et al. | 606/79 |
| 6,770,074 B2 | 8/2004 | Michelson | |
| 6,916,323 B2* | 7/2005 | Kitchens | 606/86 R |
| 7,083,623 B2 | 8/2006 | Michelson | |
| 7,207,991 B2 | 4/2007 | Michelson | |
| 7,244,258 B2* | 7/2007 | Burkus et al. | 606/90 |
| 7,326,214 B2 | 2/2008 | Michelson | |
| 7,431,722 B1 | 10/2008 | Michelson | |
| 7,491,205 B1 | 2/2009 | Michelson | |
| 7,597,695 B2* | 10/2009 | Schmiel et al. | 606/90 |
| 7,686,805 B2 | 3/2010 | Michelson | |
| 7,686,807 B2* | 3/2010 | Padget et al. | 606/86 R |
| 7,717,917 B2* | 5/2010 | Kofoed | 606/86 R |
| 7,722,619 B2 | 5/2010 | Michelson | |
| 7,771,475 B2 | 8/2010 | Michelson | |
| 7,905,884 B2* | 3/2011 | Simonton et al. | 606/79 |
| 7,909,832 B2* | 3/2011 | Michelson | 606/90 |
| 7,914,530 B2 | 3/2011 | Michelson | |
| 7,918,855 B2 | 4/2011 | Michelson | |
| 7,955,360 B2 | 6/2011 | Michelson | |
| 7,972,365 B2 | 7/2011 | Michelson | |
| 7,993,347 B1 | 8/2011 | Michelson | |
| 7,998,143 B2 | 8/2011 | Michelson | |
| 8,066,707 B2 | 11/2011 | Michelson | |
| 8,066,709 B2 | 11/2011 | Michelson | |
| 8,066,710 B2* | 11/2011 | Estes et al. | 606/90 |
| 8,328,716 B2* | 12/2012 | Schmieding et al. | 600/184 |
| 8,343,189 B2* | 1/2013 | Assell et al. | 606/247 |
| 8,372,076 B2* | 2/2013 | Simonton et al. | 606/79 |
| 8,403,841 B2* | 3/2013 | Miles et al. | 600/214 |
| 8,449,463 B2* | 5/2013 | Nunley et al. | 600/227 |
| 8,480,676 B2* | 7/2013 | Lyon | 606/86 R |
| 8,496,709 B2* | 7/2013 | Schell et al. | 623/17.16 |
| 8,535,322 B1* | 9/2013 | Powlan | 606/89 |
| 8,617,167 B2* | 12/2013 | Weisel et al. | 606/86 R |
| 8,641,719 B2* | 2/2014 | Gephart et al. | 606/86 A |
| 8,721,536 B2* | 5/2014 | Marino et al. | 600/203 |
| 8,753,345 B2* | 6/2014 | McCormack et al. | 606/79 |
| 8,795,167 B2* | 8/2014 | Ainsworth et al. | 600/222 |
| 2002/0032447 A1* | 3/2002 | Weikel et al. | 606/86 |
| 2003/0032865 A1 | 2/2003 | Estes et al. | 600/226 |
| 2004/0024408 A1* | 2/2004 | Burkus et al. | 606/90 |
| 2004/0068264 A1 | 4/2004 | Treace | 606/86 |
| 2005/0143825 A1* | 6/2005 | Enayati | 623/17.16 |
| 2005/0261681 A9* | 11/2005 | Branch et al. | 606/61 |
| 2005/0261684 A1* | 11/2005 | Shaolian et al. | 606/61 |
| 2006/0084992 A1 | 4/2006 | Michelson | 606/61 |
| 2006/0200238 A1 | 9/2006 | Schmiel et al. | 623/17.11 |
| 2007/0055379 A1* | 3/2007 | Stone et al. | 623/17.16 |
| 2007/0233252 A1* | 10/2007 | Kim | 623/17.11 |
| 2007/0270875 A1* | 11/2007 | Bacher et al. | 606/90 |
| 2008/0071279 A1* | 3/2008 | Bandeira et al. | 606/90 |
| 2008/0108875 A1* | 5/2008 | Kunkel et al. | 600/204 |
| 2008/0140013 A1* | 6/2008 | Kunkel et al. | 604/175 |
| 2008/0255667 A1* | 10/2008 | Horton | 623/17.16 |
| 2009/0125030 A1* | 5/2009 | Tebbe et al. | 606/90 |
| 2009/0131986 A1* | 5/2009 | Lee et al. | 606/247 |
| 2009/0138053 A1* | 5/2009 | Assell et al. | 606/301 |
| 2009/0143863 A1* | 6/2009 | Perez-Cruet | 623/17.16 |
| 2009/0164020 A1* | 6/2009 | Janowski et al. | 623/17.16 |
| 2009/0171389 A1* | 7/2009 | Sankaran | 606/246 |
| 2009/0265007 A1* | 10/2009 | Colleran | 623/17.16 |
| 2009/0306671 A1* | 12/2009 | McCormack et al. | 606/90 |
| 2010/0160984 A1* | 6/2010 | Berry et al. | 606/86 A |
| 2010/0174147 A1* | 7/2010 | Miles et al. | 600/202 |
| 2010/0174148 A1* | 7/2010 | Miles et al. | 600/202 |
| 2010/0191241 A1* | 7/2010 | McCormack et al. | 606/83 |
| 2010/0191296 A1* | 7/2010 | Lyon | 606/86 R |
| 2010/0198226 A1* | 8/2010 | Estes et al. | 606/90 |
| 2010/0217088 A1* | 8/2010 | Heiges et al. | 600/207 |
| 2010/0241124 A1* | 9/2010 | Housman et al. | 606/80 |
| 2011/0028791 A1* | 2/2011 | Marino et al. | 600/203 |
| 2011/0032078 A1 | 2/2011 | Guziel et al. | |
| 2011/0040154 A1* | 2/2011 | Reznik | 600/227 |
| 2011/0054537 A1* | 3/2011 | Miller et al. | 606/279 |
| 2011/0106186 A1* | 5/2011 | Wolfson | 606/86 R |
| 2011/0152866 A1* | 6/2011 | Knutson | 606/80 |
| 2011/0196494 A1* | 8/2011 | Yedlicka et al. | 623/17.16 |
| 2011/0213432 A1* | 9/2011 | Geist et al. | 606/86 R |
| 2011/0224742 A1* | 9/2011 | Weisel et al. | 606/86 R |
| 2011/0238184 A1* | 9/2011 | Zdeblick et al. | 623/17.16 |
| 2011/0251461 A1* | 10/2011 | Gomez Gonzalez et al. | 600/201 |
| 2012/0071984 A1* | 3/2012 | Michelson | 623/17.16 |
| 2012/0172670 A1* | 7/2012 | Hamada | 600/219 |
| 2012/0203071 A1* | 8/2012 | Osman | 600/207 |
| 2012/0232552 A1* | 9/2012 | Morgenstern Lopez et al. | 606/45 |
| 2012/0232658 A1* | 9/2012 | Morgenstern Lopez et al. | 623/17.16 |
| 2012/0296171 A1* | 11/2012 | Lovell et al. | 600/213 |
| 2012/0323331 A1* | 12/2012 | Michelson | 623/17.16 |
| 2013/0006364 A1* | 1/2013 | McCormack et al. | 623/17.16 |
| 2013/0013000 A1* | 1/2013 | Ainsworth et al. | 606/279 |
| 2013/0013070 A1* | 1/2013 | McCormack et al. | 623/17.16 |
| 2013/0018474 A1* | 1/2013 | McCormack et al. | 623/17.16 |
| 2013/0023995 A1* | 1/2013 | McCormack et al. | 623/17.16 |
| 2013/0023996 A1* | 1/2013 | McCormack et al. | 623/17.16 |
| 2013/0030532 A1* | 1/2013 | McCormack et al. | 623/17.16 |
| 2013/0103103 A1* | 4/2013 | Mire et al. | 606/86 A |
| 2013/0150678 A1* | 6/2013 | Miles et al. | 600/202 |
| 2013/0184771 A1* | 7/2013 | Geist | 606/86 A |
| 2013/0190769 A1* | 7/2013 | Morgenstern Lopez et al. | 606/90 |
| 2013/0310943 A1* | 11/2013 | McCormack et al. | 623/17.16 |
| 2013/0338674 A1* | 12/2013 | Geist et al. | 606/103 |
| 2013/0345667 A1* | 12/2013 | Lyon | 604/506 |
| 2013/0345712 A1* | 12/2013 | Geist et al. | 606/96 |
| 2014/0031874 A1* | 1/2014 | Kucharzyk et al. | 606/279 |
| 2014/0067069 A1* | 3/2014 | Lopez | 623/17.16 |
| 2014/0074170 A1* | 3/2014 | Mertens et al. | 606/279 |
| 2014/0100657 A1* | 4/2014 | McCormack et al. | 623/17.11 |
| 2014/0100660 A1* | 4/2014 | Morgenstern Lopez et al. | 623/17.16 |
| 2014/0114360 A1* | 4/2014 | Gephart et al. | 606/279 |
| 2014/0121467 A1* | 5/2014 | Vayser et al. | 600/214 |
| 2014/0180418 A1* | 6/2014 | Janowski et al. | 623/17.16 |
| 2014/0214165 A1* | 7/2014 | Schell et al. | 623/17.11 |

OTHER PUBLICATIONS

Hanna, A., "The Alex Hanna mobile app", Internet article: http://www.appszoom.com/iphone-apps/reference/alex-hanna-pa__evltp.html, (retrieved Mar. 18, 2013).

Bensen & Bingham, "24 Hour ticket power traffic ticket attorney", Las Vegas, Nevada, Internet Article: http://24hourticketpower.com, (retrieved Mar. 18, 2013).

Ziu, I. "Parking ticket pundit NYC iPhone", Internet article: http://www.appszoom.com/iphone-apps/utilities/parking-ticket-pundit-nyc_dlhtb.html, (retrieved Mar. 19, 2013).

Anonymous, "No traffic tickets. How to get out of a traffic ticket! 2.1.7 App for iPad, iPhone . . . ", Internet article: http://appfinder.lisisoft.com/app/no-traffic-tickets-how-to.html, (retrieved Mar. 18, 2013).

Anonymous, "Backseat lawyer", Internet article: http://udm4.com/iPhone/Backseat_Lawyer-3621608, (retrieved Mar. 18, 2013).

Bharath, M., "Fight your ticket 1.1 App for iPad, iPhone, Medical", Internet article: http://appfinder.lisisoft.com/app/fight-your-ticket.html, (retrieved Mar. 18, 2013).

Anonymous, "Pocket attorney app. a lawyer in your pocket", Internet article: http://pocketattorneyapp.com, (retrieved Mar. 18, 2013).

Rand, "Babkes law iPhone", Internet article: http://www.appszoom.com/iphone-apps/business/babkes-law__eumjc.html, (retrieved Mar. 19, 2013).

Ticketdefender LLC, "TicketDefender iPhone", Internet article: http://www.appszoom.com/iphone-apps/navigation/ticketdefender__efjcs.html, (retrieved Mar. 18, 2013).

Anonymous, "Don't pay that speeding ticket. How to fight a traffic ticket or moving radar violation", Internet article: http://www.

(56) References Cited

OTHER PUBLICATIONS appszoom.com/iphone-apps/lifestyle/dont-pay-that-speeding-ticket-how-to-fight-a-traffic-ticket-or-moving-radar-violation-in-court-a_dvcmp.html?nav=related. (retrieved Mar. 18, 2013).

Nextgenmobile, "File my tickets—Android", Internet article: http://pt.appszoom.com/android_applications/transportation/file-my-tickets_cbhwe.html, (retrieved Mar. 18, 2013).

JDG, "Fight that ticket—SlideMe v.2.8", Internet article: http://slideme.org/application/fight-ticket, (retrieved Mar. 18, 2013).

Ticketbust.com, "iTicketBust for iPhone, iPod touch, and iPad on the iTunes app store", Internet article: https://itunes.apple.com/app/iticketbust/id425364397, (retrieved Mar. 18, 2013).

Anonymous, "Mr. Ticket traffic ticket attorney mobile app", Internet article: http://www.mrtickettrafficattorney.com/mrticketmobileapp, (retrieved Mar. 18, 2013).

Anonymous, "TicketVoid fight your ticket", Internet article: http://appfinder.lisisoft.com/app/ticket-void-traffic-ticket.html, (retrieved Mar. 18, 2013).

* cited by examiner

ACCESS ASSEMBLY FOR ANTERIOR AND LATERAL SPINAL PROCEDURES

CROSS REFERENCE TO RELATED APPLICATION

In accordance with 37 C.F.R 1.76, a claim of priority is included in an Application Data Sheet filed concurrently herewith. Accordingly, under 35 U.S.C. §119(e), 120, 121, and/or 365(c) the present invention claims priority of U.S. Patent Application No. 61/585,724, entitled "ACCESS ASSEMBLY FOR ANTERIOR AND LATERAL SPINAL PROCEDURE", filed on Jan. 12, 2012. The contents of each of the above referenced applications are herein incorporated by reference in its entirety.

FIELD OF INVENTION

The present invention relates generally to stabilization of adjacent bony structures of the spine and more particularly to an assembly and method for providing anterior and/or lateral access to the disc space of the vertebrae for providing stabilization to the bony structures thereof.

BACKGROUND INFORMATION

It is widely held that healing and/or structural correction is greatly facilitated when a bone is stabilized in the proper position. Various devices for stabilization of bone are well known and routinely practiced in the medical arts. For example, an abnormal spine can be stabilized using a substantially rigid or semi-rigid interconnecting means (rod or plate) and fastening means (screws, clamps, hooks, claws, anchors, or bolts). Multiple fasteners are placed into the spinal pedicle of each vertebra and linked by at least one interconnecting means. Once in place, these systems substantially immobilize the spine and promote bony fusion (arthrodesis).

With respect to the thoracic spine, it may be afflicted with a variety of ailments, some so severe as to require surgical intervention. A disc herniation may compress the spinal cord and/or nerve roots and cause pain, loss of function, and even complete paralysis of the legs with loss of bowel and bladder control. The correct treatment for such conditions is the removal of the offending discal tissue. However, this has proven both difficult and quite dangerous. When the discs of the thoracic spine are approached posteriorly (from behind), the spinal cord is in the way. To approach the same herniation anteriorly (from the front) requires the very formidable procedure of thoracotomy (cutting open the chest) and moving the heart and lungs out of the way.

Quite recently surgeons have begun performing these procedures from a lateral approach to the spine (from the side) using fiber optic viewing instruments called thorascopes and numerous small surgical openings through the chest wall (portals) through which various surgical instruments, such as burrs, rongeurs and curettes, may be placed to remove these disc herniations while avoiding formal thoracotomy. Because the discs are very narrow in the thoracic spine and the surgeon is approaching the spine laterally, there is very little space in which to work as the disc is entered. Therefore, the amount of disc removal may be limited. Alternatively, the surgeon might remove the pedicle to gain access to the spinal canal risking further weakening of the already diseased area.

Sometimes, for a variety of reasons, including the removal of disc material, the thoracic spine may become unstable (too much motion) at any given level. Historically, this has been treated by fusion, the joining together permanently of the unstable vertebrae via a bridge of bone so as to eliminate all motion at that location. Fusions about the thoracic spine have been performed either anteriorly or posteriorly, either procedure being a serious surgical undertaking.

Stability of the spine is required for fusion to occur. For this reason, and for the purpose of correcting spinal deformity, it is often necessary to use hardware to rigidly internally fixate (stabilize) the spine. To date, the only benefit the use of the thorascope has provided in this regard is to allow the previous thoracotomy incision to be somewhat smaller.

Thus, the prior art includes numerous drawbacks which have not been entirely addressed. Traditionally, the surgical techniques for stabilization of bone required large incisions (upwards of 6 cm in length) and a considerable amount of muscle be cut and stripped away (retracted) from the bone for an "open" visualization of the bone and access thereto for the placement of the fasteners and instrument implantation. Although this so-called "open" surgical technique has successfully treated non-unions, instability, injuries and disease of the spine, it is not without disadvantages. Given the invasive nature of this technique, a lengthy healing time and considerable post-operative pain for the patient is common.

With respect to the human lumbar spine, the treatment of discal disease with neural compression has generally been from a posterior (from behind) approach. Lumbar discs are generally quite large and it is only those protrusions occurring posteriorly which compress the neural elements, which are themselves posterior to the discs. These posterior approaches have included both true posterior approaches and posterolateral approaches to the discs. Further, such approaches have been made via open incisions or through percutaneous stab wounds. In the latter case, instruments are inserted through the stab wounds and monitored by the use of radiographic imaging or the use of an endoscopic viewing device. While it is possible to also decompress a posterior disc herniation in the lumbar spine from an anterior approach (from the front), doing so requires the removal of a very substantial portion or all of the disc material in the front and mid portions of the disc, thus leaving that disc and that spinal segment generally unstable. Therefore, such an anterior approach to the lumbar spine has been reserved for those instances where a fusion is to be performed in conjunction with, and following such a disc removal.

Fusion is generally induced with the application of bone or bone like substances between bones to induce bony bridging; such procedures have been performed outside the vertebral bodies and/or between the vertebral bodies, the latter being known as an interbody fusion. Such interbody fusions have been performed from posterior, posterolateral and anterior. Interbody fusion from the posterior approach, while still in use, has been associated with significant complications generally related to the fact that the delicate dural sac and the spine nerves cover the back of the disc space and are thus clearly at risk for damage with such an approach. The posterolateral approach has generally been utilized as a compliment to percutaneous discectomy and has consisted of pushing tiny fragments of morsalized bone down through a tube and into the disc space.

In anterior interbody spinal fusion, the path of entry of the fusion material into the intervertebral space is performed from a straight anterior position. Such an anterior position is achieved in one of two ways. First, by a straight anterior approach which requires that the peritoneal cavity, which contains the intestines and other organs, be punctured twice, once through the front and once through the back on the way to the front of the spine; or secondly, by starting on the front of the abdomen off to one side and dissecting behind the peritoneal cavity on the way to the front of the spine. Regardless of which approach to the front of the spine is used, and apart from the obvious dangers related to the dense anatomy and vital structures in that area, there are at least two major problems specific to the anterior interbody fusion angle of implant insertion itself. First, generally at the $L_4$ and $L_5$ discs, the great iliac vessels bifurcate from the inferior vena cava and lie in close apposition to and covering that disc space, making fusion from the front both difficult and dangerous. Secondly, anterior fusions have generally been done by filling the disc space with bone or by drilling across the disc space and then filling those holes with shaped implants. As presently practiced, the preferred method of filling the disc space consists of placing a ring of allograft (bone not from the patient) femur into that disc space. An attempt to get good fill of the disc space places the sympathetic nerves along the sides of the disc at great risk. Alternatively, when the dowel technique is used, because of the short path from the front of the vertebrae to the back and because of the height of the disc as compared to the width of the spine, only a portion of the cylindrical implant or implants actually engage the vertebrae; thus compromising the support provided to the vertebrae and the area of contact provided for the fusion to occur.

There is, therefore, in regard to the lumbar spine, a need for a new method and apparatus for achieving interbody fusion which avoids the problems associated with all prior methods, and which have included, but are not limited to, nerve damage when performed posteriorly, or the need to mobilize the great vessels when performed anteriorly. Further, the size of the implants are limited by the dural sac posteriorly, and the width of the spine and the delicate vital structures therewith associated anteriorly. Such a method and apparatus for interbody fusion should provide for optimal fill of the interspace without endangering the associated structures, and allow for the optimal area of contact between the implant or implants and the vertebrae to be fused. The method and apparatus should also provide controlled distraction of the bony structures while also providing an interlocking connection to the bony structures to prevent movement or dislodgement of the apparatus.

SUMMARY OF THE INVENTION

Briefly, the present invention is directed to methods and instrumentation for performing surgery on the spine along its lateral aspect (side), and generally by a lateral, anterior or an anterolateral surgical approach, such that the instruments enter the body from an approach that is other than posterior and make contact with the spine along its lateral aspect. The present invention provides for the entire surgical procedure to be performed through a relatively small incision and may be performed in either the thoracic or lumbar spine.

In the preferred embodiment, the access assembly of the present invention comprises a guide wire, a distractor, and a dynamic tube assembly that includes a manually operable locking member for securing the dynamic tube assembly to the bony structure. In at least one embodiment, the locking feature of the dynamic tube assembly may also be utilized for providing additional controlled distraction of the bony structures. The guide wire is provided for initial insertion into the disc space through a small incision in the patient with the assistance of x-rays, thorascope, image intensifier, direct vision or the like. For example, for surgery in the thoracic spine, a small incision in the chest cavity of the patient is made from a lateral approach to the thoracic spine. For surgery in the lumbar spine, a small incision may be made in the abdominal wall of the patient. Once positioned, the guide wire extends between the disc space to outside of the patient to provide a guideway for the distractor member. The distractor is generally an elongated member having a small central aperture sized for cooperation with the guide wire. A first end of the distractor includes a tapered end and a pair of generally flat opposing side surfaces extending along a portion of the length thereof. The opposing side surfaces are spaced a predetermined distance apart to provide a desired distraction (spacing) and alignment of the vertebrae. The second end of the distractor is provided with a surface suitable for striking with a mallet or the like. The outer surface of the distractor is preferably round to act as a guide surface for the dynamic tube assembly.

The dynamic tube assembly includes an outer tube member and an inner lock member. The inner lock member includes an inner bore sized for cooperation with the outer surface of the distractor member. In this manner, the distractor acts as a guideway for the dynamic tube assembly. The dynamic tube assembly is constructed and arranged so that a portion of the lock member and outer tube member extend a short distance into the disc space adjacent the side surfaces of the distractor and between the two opposed surfaces. The lock member is then rotatable to engage the opposing bony surfaces of the disc space. In this manner, the lock member secures the first end of the dynamic tube assembly into place and releases the distractor member for extraction from the patient through the bore of the dynamic tube assembly. In some embodiments the lock member may include a shaped cam surface that provides additional controlled distraction of the disc space during rotation thereof. The locking function prevents the first end of the dynamic tube assembly from being inadvertently moved from its intended position once placed, while maintaining the adjacent vertebrae in a distracted position and aligned position. Once the dynamic tube assembly is in place within the patient, the distractor and guide wire may be removed, providing an access tunnel to the disc space. The tunnel is provided with sufficient diameter for disc modification or removal as well as the placement of spacers, bone fragments, implants and the like to be passed therethrough to the disc space. Once the operation is completed, rotation of the lock member releases the dynamic tube assembly for removal from the patient.

Accordingly, it is an objective of the present invention to provide a device and method for performing surgery on the thoracic spine through the chest cavity from a lateral approach to the spine.

It is a further objective of the present invention to provide a device and method for performing a thoracic discectomy, an interbody fusion, and rigid internal fixation of the spine through the chest cavity from a lateral approach as a single integrated procedure.

It is yet a further objective of the present invention to provide a device and method for performing a lumbar fusion from the lateral aspect of the spine.

It is another objective of the present invention to provide a method and device for performing a lumbar fusion and spinal canal decompression from the lateral aspect of the spine.

It is yet another objective of the present invention to provide a device and method for performing a lumbar fusion, decompressive discectomy, and a rigid internal fixation of the spine as a single integrated surgical procedure.

It is still yet another objective of the present invention to provide a device and method to achieve discectomy, fusion and interbody stabilization of the lumbar without the need to mobilize the great vessels from the front of the vertebral bodies.

It is still yet another objective of the present invention to provide a device for performing surgery on the spine that includes a controlled locking mechanism for securing the surgical device to the bony structure.

It is still yet another objective of the present invention to provide a device for performing surgery on the spine that includes a cam surface for providing controlled distraction of a disc space.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENTS

Figure 1:
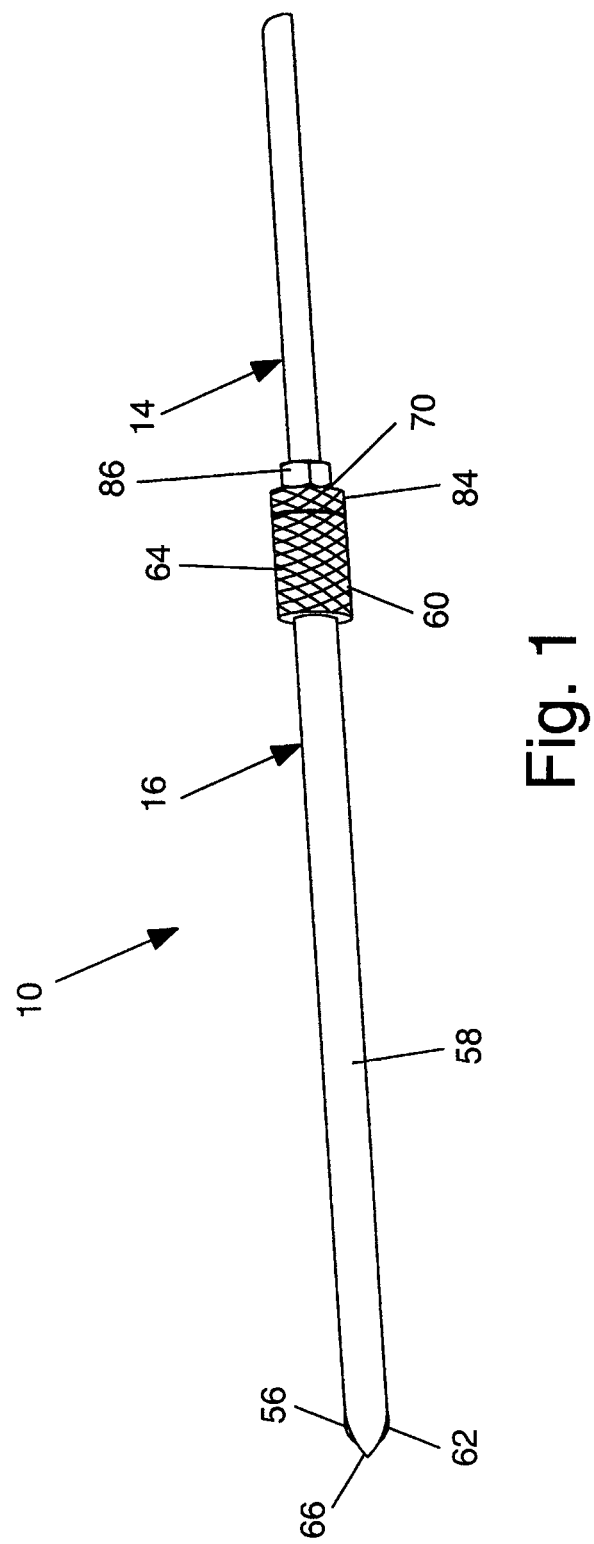
FIG. 1 is a perspective view of one embodiment of the present invention.
Figure 2:
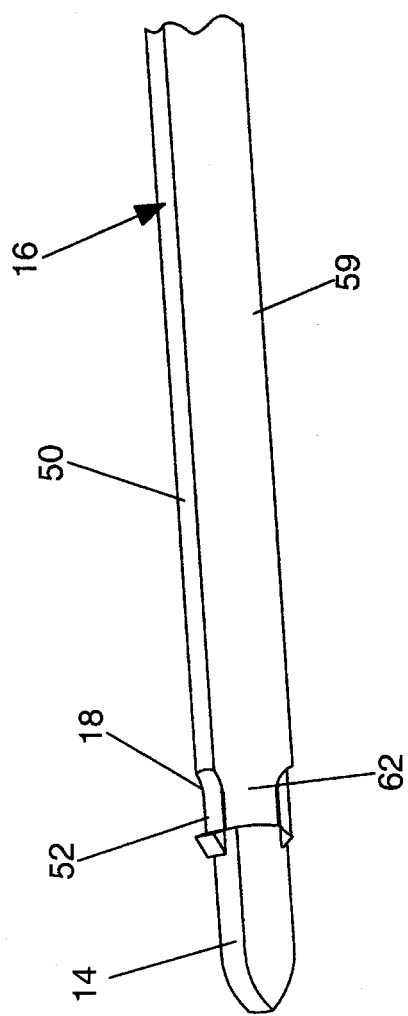
FIG. 2 is a partial perspective view of the embodiment shown in FIG. 1 illustrating the first end thereof.
Figure 3:
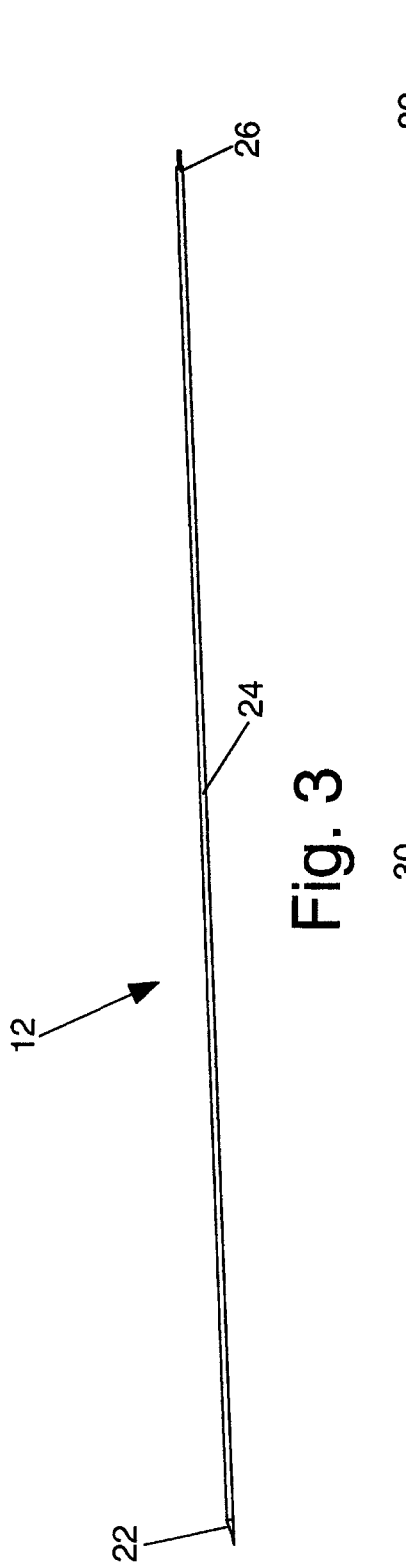
FIG. 3 is a perspective view of one embodiment of the guide wire of the present invention.
Figure 4:
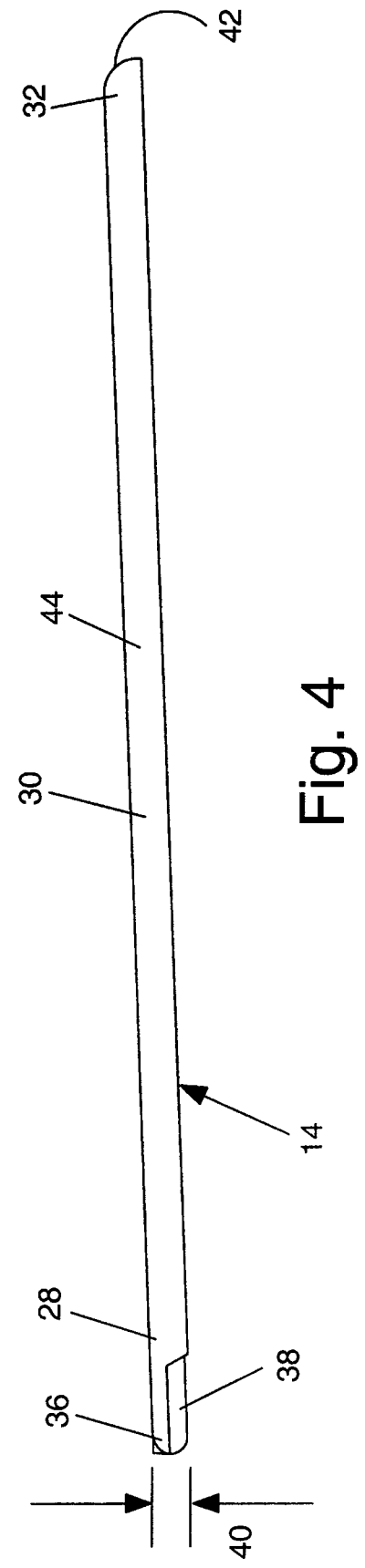
FIG. 4 is a perspective view of one embodiment of the distractor member of the present invention.
Figure 5:
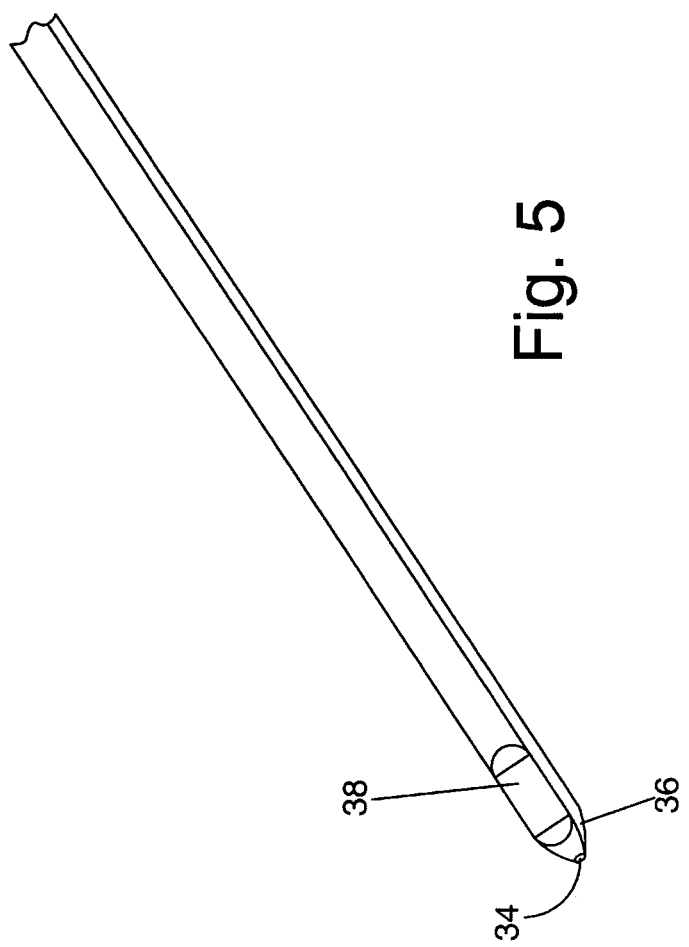
FIG. 5 is a partial perspective view of the first end of the distractor member illustrated in FIG. 4.
Figure 6:
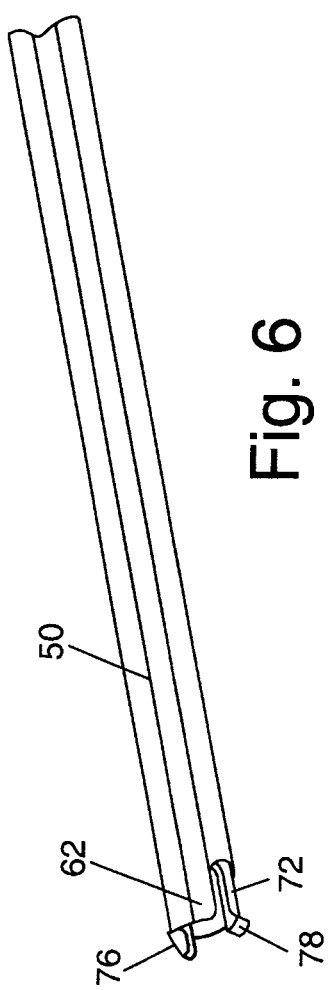
FIG. 6 is a partial perspective view of one embodiment of the dynamic tube assembly of the present invention.
Figure 7:
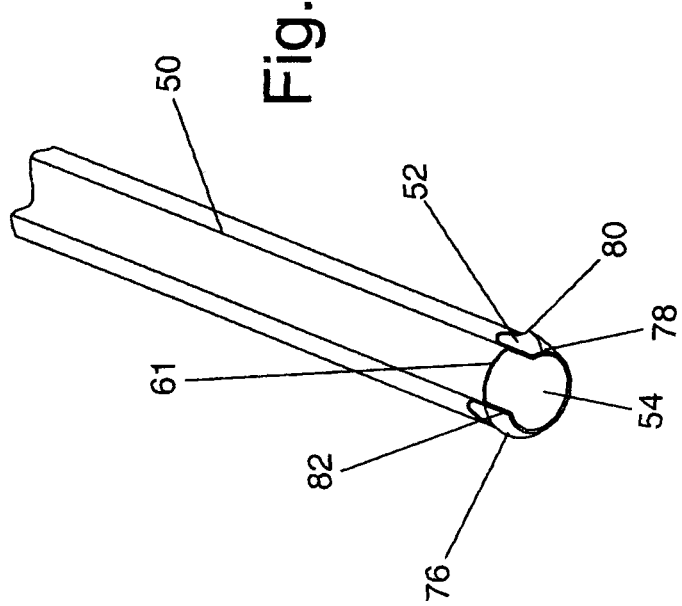
FIG. 7 is a partial perspective view of the dynamic tube assembly shown in FIG. 6 illustrating the locking member positioned in the locking position.
Figure 8:
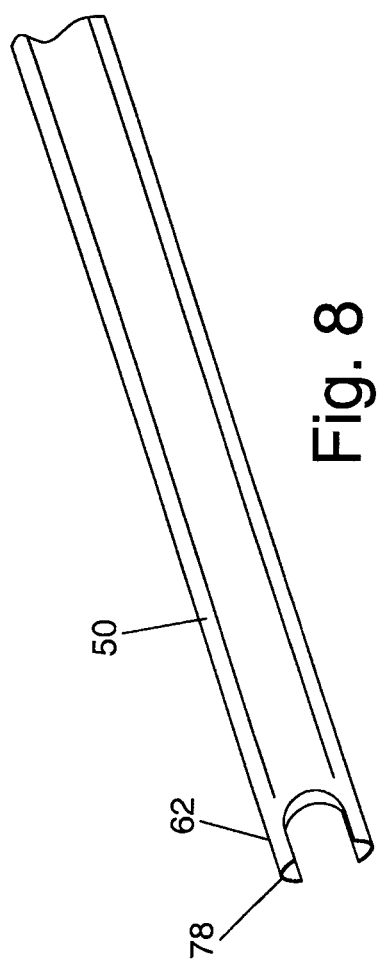
FIG. 8 is a partial perspective view of the dynamic tube assembly shown in FIG. 6 illustrating the locking member positioned in the unlocked position.
Figure 9:
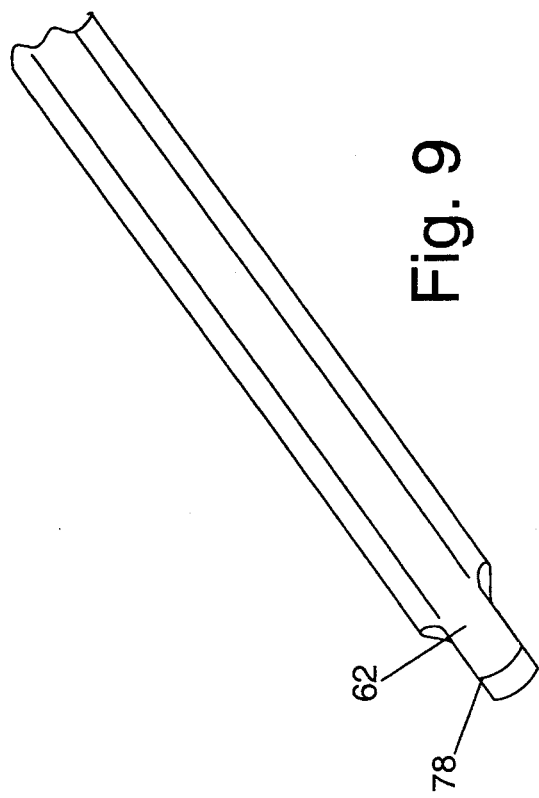
FIG. 9 is a partial perspective view of the dynamic tube assembly shown in FIG. 6 illustrating the locking member positioned in the unlocked position.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to FIGS. 1-16, an access assembly 10 constructed and arranged for anterior, lateral anterolateral spinal procedures is illustrated. The present invention provides for the entire surgical procedure to be performed through a relatively small incision, and may be performed in either the thoracic or lumbar spine. In the preferred embodiment, the access assembly 10 comprises a guide wire 12, a distractor 14, and a dynamic tube assembly 16 that includes a manually operable locking member 18 for securing the dynamic tube assembly to a bony structure.

Figure 10:
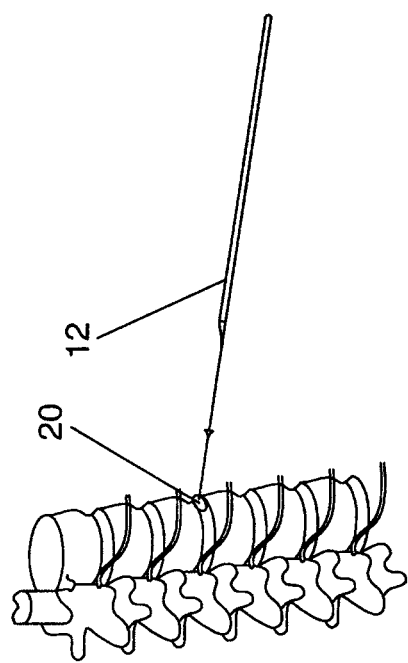
FIG. 10 is a perspective view of a segment of the thoracic spine and of the guide wire of the present invention being inserted from a lateral approach into the disc space between two adjacent vertebrae.
Figure 11:
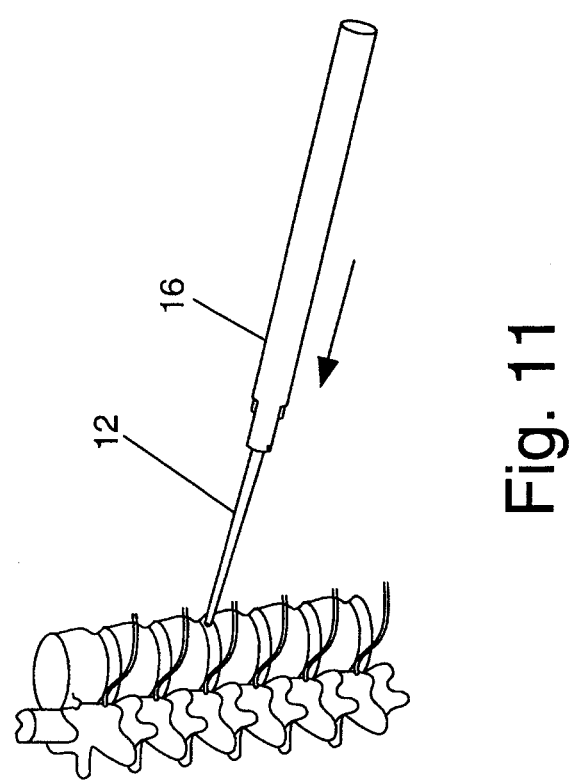
FIG. 11 is a perspective view of the distractor member being inserted over the guide wire of FIG. 10.
Figure 12:
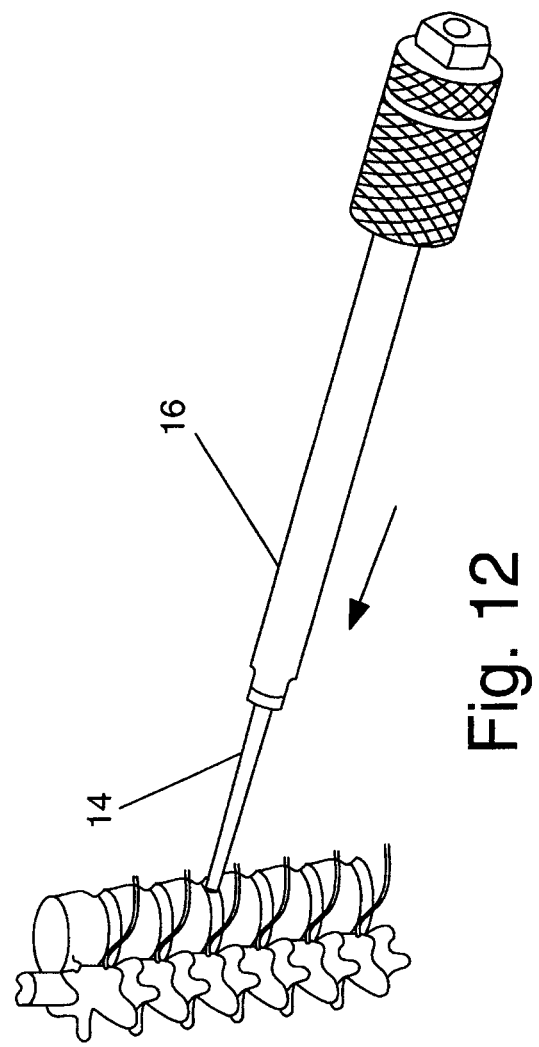
FIG. 12 is a perspective view of the dynamic tube assembly being inserted over the distractor member of FIG. 11.
Figure 13:
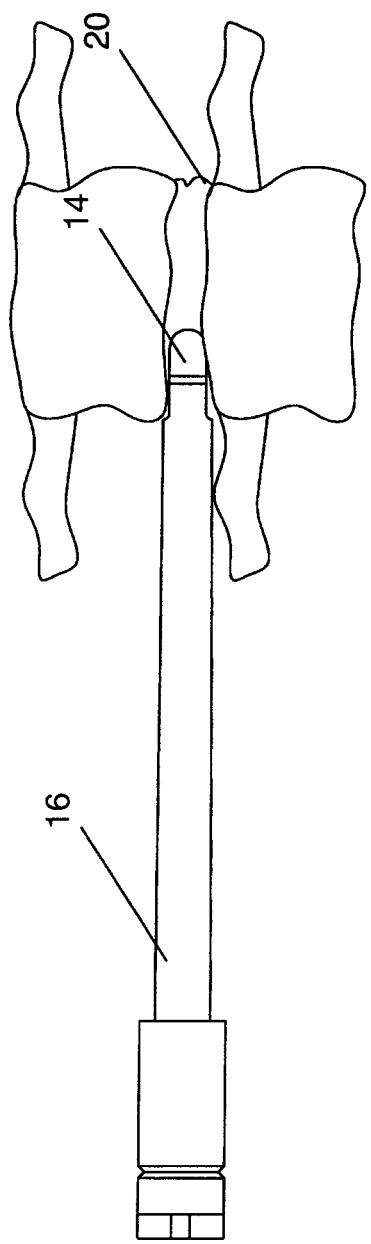
FIG. 13 is a front view of a portion of the segment of thoractic spine shown in FIG. 1 illustrating the dynamic tube assembly fully seated into the disc space over the distractor member with the locking member in the unlocked position.
Figure 14:
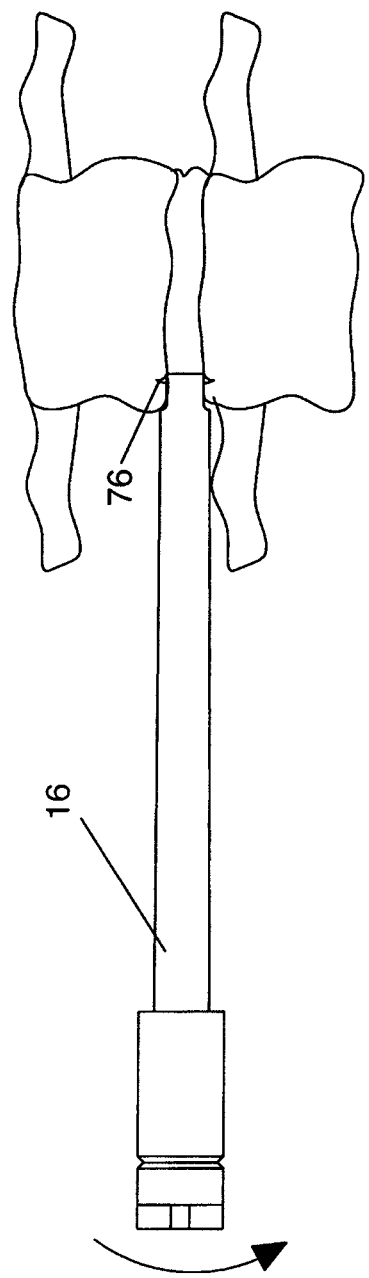
FIG. 14 is a front view of the segment of the thoracic spine shown in FIG. 13 illustrating the locking member in the locked position with the distractor member removed.
Figure 16:
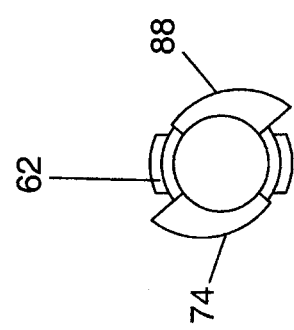
FIG. 16 is an end view of one embodiment of the dynamic tube assembly.
Figure 15:
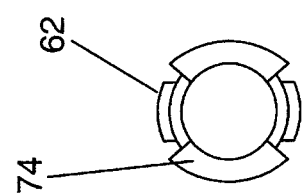
FIG. 15 is an end view of one embodiment of the locking dynamic tube assembly.

The guide wire 12 is provided for initial insertion into the disc space through a small incision in the patient with the assistance of x-rays, thorascope, image intensifier, direct vision or the like, see FIG. 10. For example, for surgery in the thoracic spine, a small incision in the chest cavity of the patient is made from a lateral approach to the thoracic spine. For surgery in the lumbar spine, a small incision may be made in the abdominal wall of the patient. The first end 22 of the guide wire 12 may be inserted with the assistance of a jam shidi needle or other suitable cannula. Alternatively, the guide wire may have sufficient rigidity for direct insertion. The first end 22 of the guide wire 12 may include a particular shape that aids in the insertion such as, but not limited to, a conical point, trocar, spherical or blunt. Once positioned, the central shaft 24 of the guide wire 12 extends between the disc space to outside of the patient to provide a guideway for the distractor member. The second end 26 of the guide wire 12 generally includes a blunt square cut. The guide wire 12 is preferably constructed from a biocompatible metal material such as spring temper stainless steel or nitinol. However, it should be noted that any material having sufficient rigidity to act as a guideway for the distractor member may be utilized without departing from the scope of the invention.

The distractor 14 is generally an elongated member having a first end 28, a central portion 30 and a second end 32. Extending through a central portion of the distractor is a small central aperture 34 sized for cooperation with the outer surface of the center portion of the guide wire 12. The first end of the distractor preferably includes a tapered end 36 for ease of insertion into the disc space. In a most preferred embodiment, the tapered end includes a frustoconical shape. However, it should be noted that other shapes may be utilized for the tapered end so long as they provide a smooth transition from the outer diameter of the guide wire to the outer diameter of the distractor. Such shapes may include, but should not be limited to, spherical, bullet, pyramid or suitable combinations thereof. A pair of generally flat opposing side surfaces 38 extend along a portion of the length of the center portion 30. The opposing side surfaces are spaced a predetermined distance apart 40, which may include a taper, to provide a desired distraction (spacing) and alignment of the vertebrae. The second end 32 of the distractor 14 is provided with a surface 42 suitable for striking with a mallet or the like. The outer surface 44 of the distractor is preferably round to act as a guide surface for the dynamic tube assembly. It should be noted that while the inner and outer surfaces of the distractor member are illustrated as being round, other matched shapes may be utilized without departing from the scope of the invention.

The dynamic tube assembly 16 includes an outer tube member 50 and an inner lock member 52. The dynamic tube assembly 16 includes a first end 56, a center portion 58, a second end 60, an outer surface 59 and an inner surface 61. The first end 56 includes a pair of tab members 62 integrally formed thereto and sized so that they extend a short distance into the disc space adjacent the distractor and between the two opposed surfaces. In this manner, the dynamic tube assembly may be easily traversed to its desired functional position. The second end 60 of the dynamic tube assembly 16 includes a gripping portion 64 for providing counter-rotation force to the dynamic tube assembly during actuation of the lock member 52. The inner surface of the outer tube member is sized to cooperate with the outer surface of the locking member so as to function as a bearing surface for rotation of the lock member.

The inner lock member 52 extends through the inner bore 54 of the outer tube member 50 and includes a first end 66, a center portion (not shown), a second end 70, an inner bore 54, and an outer surface 72. The first end of the lock member preferably includes at least two locks 74 extending beyond and having approximately the same width as the tabs 62, whereby the lock member may be rotated to align substantially therewith for insertion alongside the distractor. The distal ends of the locks each include at least one barb portion 76 which may include a ramp portion 78, a rear surface 80 and a pair of side surfaces 82. The ramp portion 78 provides easy entry through tissue and the like, while the side surfaces 82 may be constructed and arranged to bite and/or cut into the bone during rotation to create a secure engagement. The center portion 68 of the lock member is sized and shaped to cooperate with the inner surface 61 of the outer tube member 50 to allow free rotation therebetween. The second end 70 of the lock member 52 extends through the outer tube member terminating in a second gripping portion 84 which may include a hex 86 of shape constructed and arranged for providing rotational torque to the lock member for engagement or disengagement thereof. The inner bore 54 is sized for cooperation with the outer surface 44 of the distractor member 14. In this manner, the distractor acts as a guideway for the dynamic tube assembly. The lock member is then rotatable to engage the opposing bony surfaces of the disc space. In this manner, the lock member secures the first end of the dynamic tube assembly into place and releases the distractor member for extraction from the patient while maintaining the adjacent vertebrae in a distracted and aligned position. In some embodiments the lock member may include a shaped cam surface 88 that provides additional controlled distraction of the disc space during rotation thereof. Once the dynamic tube assembly is in place within the patient, the distractor and guide wire may be removed providing an access tunnel to the disc space. The tunnel is provided with sufficient diameter for disc modification or removal as well as the placement of spacers, bone fragments, implants and the like to be passed therethrough to the disc space. Once the operation is completed, rotation of the lock member releases the dynamic tube assembly for removal from the patient.

What is claimed is:

1. An access assembly kit for spinal procedures comprising:
    a guide wire (12) for insertion into a disc space of a spine, said guide wire having sufficient length to extend from said disc space to a position outside of the body, said guide wire constructed of a material having sufficient rigidity to act as a guideway for a distractor member (14);
    said distractor member (14), being a generally elongated member having a first end (28), a central portion (30) and a second end (32), said distractor member (14) having an aperture extending through a central portion thereof for closely sized sliding cooperation with an outer surface of said guide wire (12), said first end (28) of said distractor member (14) being tapered for insertion into said disc space, whereby said first end is constructed and arranged to contact and cause distraction of two opposed bony structures;
    a dynamic tube assembly (16) that includes a manually operable locking member (18) for securing said dynamic tube assembly (16) to at least one of two opposed bony structures adjacent to said disc space said dynamic tube assembly (16) includes a first end (56), a center portion (58), a second end (60), an outer surface (59) and an inner surface (61), said first end (56) including a pair of tab members (62) integrally formed thereto and sized to extend a short distance into said disc space adjacent said distractor and between said two opposed bony structures, a lock member (52) secured for rotation within said outer tube member (50) and extending through said inner surface (61) of an outer tube member (50) and includes a first end (66), a center portion, a second end (70), said inner surface (61), and an outer surface (72), said first end (66) of said lock member (52) includes at least two locks (74) extending beyond and having approximately the same width as said tab members (62), whereby said lock member may be rotated to align substantially therewith for insertion alongside said distractor member (14) between said opposed bony structures and whereby said lock member may be rotated to a position between said distractor member and said opposed bony structures to maintain said distraction of said opposed bony structure while said distractor member is removed.

2. The access assembly kit for spinal procedures of claim 1 wherein said inner surface (61) of said outer tube member (50) is sized to cooperate with an outer surface of said inner lock member (52) so as to function as a bearing surface for rotation of said inner lock member (52).

3. The access assembly kit for spinal procedures of claim 1 wherein said distal ends of said at least two locks (74) each include at least one barb portion (76), a rear surface (80), and a pair of side surfaces (82), said at least one barb portion being constructed and arranged to engage at least one of said at least two opposed bony structures.

4. The access assembly kit for spinal procedures of claim 3 wherein each of said at least one barb portions (76) include a ramp portion (78), each said ramp portion (78) providing easy entry through tissue and the like, said side surfaces (82) constructed and arranged to bite or cut into said bone during rotation to create a secure engagement therebetween.

5. The access assembly kit for spinal procedures of claim 3 wherein each of said locks include a shaped cam surface (88) that provides additional controlled distraction of said disc space during rotation thereof.

6. The access assembly kit for spinal procedures of claim 1 wherein said second end (70) of said lock member (52) extends through said outer tube member (50) terminating in a second gripping portion (84) constructed and arranged for providing rotational torque to said lock member for engagement or disengagement thereof.

7. The access assembly kit for spinal procedures of claim 6 wherein said second end (70) of said lock member (52) includes a polygon shape (86) for providing rotational torque to said lock member for engagement or disengagement thereof.

8. The access assembly kit for spinal procedures of claim 1 wherein said second end (60) of said dynamic tube assembly (16) includes a gripping portion (64) for providing counter-rotation force to the dynamic tube assembly during actuation of the lock member (52).

9. The access assembly kit for spinal procedures of claim 1 wherein said distractor member includes a pair of generally flat opposing side surfaces (38) extending along a portion of the length of said central portion (30), said opposing side surfaces (38) being spaced a predetermined distance apart (40), to provide a desired distraction and alignment of said two opposed bony structures.

10. The access assembly kit for spinal procedures of claim 9 wherein said pair of generally flat opposing side surfaces (38) include a taper to provide a desired distraction and alignment of said two opposed bony structures.

11. The access assembly kit for spinal procedures of claim 1 wherein said second end (32) of said distractor (14) is provided with a surface (42) suitable for striking with a mallet.

12. A distractor assembly for providing access to a disc space comprising:
   a distractor member (14), said distractor being a generally elongated member having a first end (28), a central portion (30) and a second end (32), said distractor member (14) having an aperture extending through a central portion thereof for cooperation with an outer surface of said guide wire (12), said first end (28) of said distractor member (14) being tapered for insertion into a disc space;
   a dynamic tube assembly (16) that includes a manually operable locking member (18) for securing said dynamic tube assembly (16) to at least one of two opposed bony structures adjacent to said disc space, said dynamic tube assembly (16) including an outer tube member (50) and an inner lock member (52), said inner lock member (52) secured for rotation within said outer tube member (50), said dynamic tube assembly (16) including a first end (56), a center portion (58), a second end (60), an outer surface (59) and an inner surface (61), said first end (56) including a pair of tab members (62) integrally formed thereto and sized to extend a short distance into said disc space adjacent said distractor and between said two opposed bony structures, said inner lock member (52) extending through said inner bore (54) of said outer tube member (50) and including a first end (66), a center portion, a second end (70), an inner bore (54), and an outer surface (72), said first end (66) of said lock member (52) including at least two locks (74) extending beyond and having approximately the same width as said tabs (62), whereby said lock member may be rotated to align substantially therewith for insertion alongside said distractor member (14).

13. The distractor assembly of claim 12 wherein said distal ends of said at least two locks (74) each include at least one barb portion (76), a rear surface (80), and a pair of side surfaces (82), said at least one barb portion being constructed and arranged to engage at least one of said at least two opposed bony structures.

14. The access assembly kit for spinal procedures of claim 13 wherein each of said at least one barb portions include a ramp portion (78), each said ramp portion (78) providing easy entry through tissue and the like, said side surfaces (82) constructed and arranged to bite or cut into said bone during rotation to create a secure engagement therebetween.

15. The distractor assembly of claim 13 wherein each of said at least two locks include a shaped cam surface (88) adapted to provide additional controlled distraction of said disc space during rotation thereof.

16. A distractor assembly for providing access to a disc space comprising:
   a distractor member (14), said distractor being a generally elongated member having a first end (28), a central portion (30) and a second end (32), said first end (28) of said distractor member (14) being tapered for insertion into a disc space;
   a dynamic tube assembly (16) that includes a manually operable locking member (18) journalled for rotation therein for securing said dynamic tube assembly (16) to at least one of two opposed bony structures adjacent to said disc space, said dynamic tube assembly (16) including a first end (56), a center portion (58), a second end (60), an outer surface (59) and an inner surface (61), said first end (56) including a pair of tab members (62) integrally formed thereto and sized to extend a short distance into said disc space adjacent said distractor and between said two opposed bony structures, said inner lock member (52) extending through said inner bore (54) of said outer tube member (50) and including a first end (66), a center portion, a second end (70), an inner bore (54), and an outer surface (72), said first end (66) of said lock member (52) including at least two locks (74) extending beyond and having approximately the same width as said tab members (62), whereby said lock member may be rotated to align substantially therewith for insertion alongside said distractor member (14), said locking member (18) rotatable to cause said at least two locks to engage at least one of said at least two opposed bony structures.

\* \* \* \* \*